US005776700A

United States Patent [19]

Brass et al.

[11] Patent Number: 5,776,700
[45] Date of Patent: Jul. 7, 1998

[54] THROMBINE RECEPTOR ACTIVATION ASSAY FOR USE IN IDENTIFYING THROMBIN RECEPTOR ANTAGONISTS

[75] Inventors: Lawrence Brass, Bala Cynwyd, Pa.; Ram Ramachandran, Newark, Del.

[73] Assignee: Trustees of the University of Pennsylvania, Philadelphia, Pa.

[21] Appl. No.: 709,558

[22] Filed: Sep. 5, 1996

[51] Int. Cl.$^6$ ............................................... C12N 15/12
[52] U.S. Cl. ........................... 435/7.2; 424/93.1; 435/4; 435/13; 435/40.5; 436/86; 436/501; 436/811
[58] Field of Search .................... 424/93.1; 435/4, 435/7.1, 7.2, 7.9, 13, 40.5, 40.51, 240.2, 245; 436/86, 501, 50.4

[56] References Cited

FOREIGN PATENT DOCUMENTS

92/14750  9/1992  WIPO .

OTHER PUBLICATIONS

Brass, L., Homologous Desensitization of HEL Cell Thrombin Receptors, The Journal of Biological Chemistry, vol. 267, No. 9, pp. 6044–6050, 1992.

Brass et al., Structure and Function of the Human Platelet Thrombin Receptor. The Journal of Biological Chemistry, vol. 267, No. 20, pp. 13795–13798, 1992.

Brass et al., Changes in the Structure and Function of the Human Thrombin Receptor during Receptor Activation, Internalization and Recycling. The Journal of Biological Chemistry, vol. 269, No. 4, pp. 2943–2952, 1994.

Woolkalis et al., Regulation of Thrombin Receptors on Human Umbilical Vein Endothelial Cells. The Journal of Biological Chemistry, vol. 270, No. 17, pp. 9868–9875, 1995.

Vu et al., Molecular Cloning of Functional Thrombin Receptor Reveals a Novel Proteolytic Mechanism of Receptor Activation. Cell, vol. 64, pp. 1057–1068, 1991.

Vassallo et al., "Structure–Function Relationships in the Activation of Platelet Thrombin Receptors by Receptor–derived Peptides", J. Biol. Chem. 1992 267, 6081–6085.

Hoxse et al "Internalization and Recycling of Activated Thrombin Receptors" 1993, vol. 268, No. 18 pp. 13756–13763 J. of Biol. Chem.

Primary Examiner—James C. Housel
Assistant Examiner—Bao-Thuy L. Nguyen
Attorney, Agent, or Firm—Law Offices of Jane Massey Licata

[57] ABSTRACT

An assay for determining thrombin receptor activation in a cell by measuring the internalization of a labeled antibody-thrombin receptor complex following exposure to an agonist peptide is provided. This method is useful in identifying thrombin receptor antagonists.

2 Claims, 3 Drawing Sheets

THROMBINE RECEPTOR ACTIVATION ASSAY FOR USE IN IDENTIFYING THROMBIN RECEPTOR ANTAGONISTS

INTRODUCTION

This invention was made in the course of research sponsored by the National Institutes of Health. The U.S. Government may have certain rights in this invention.

BACKGROUND OF INVENTION

Thrombin receptors are members of the super-family of G protein coupled receptors. They have a structure comprised of a single polypeptide chain with an extracellular N-terminus and seven transmembrane domains. Unlike many other members of this family, however, thrombin receptors are activated by an irreversible event that begins when thrombin cleaves the $Arg^4Ser^{42}$ bond in the receptor's N-terminus, exposing a neo-N-terminus containing the tethered ligand domain (SFLLR. . . .). Synthetic peptides corresponding to this domain are able to serve as receptor agonists, giving rise to a family of "agonist peptides" that are effective in the μM range. Because thrombin receptor activation is an irreversible event, most cells have evolved mechanisms for rapidly clearing activated receptors from their surface and then slowly replacing them with intact receptors. The internalization process involves coated pits in the plasma membrane which are believed to be triggered by receptor activation.

Thrombin and thrombin receptors are important in the development of the platelet plug and fibrin clot that are normally formed during vascular injury. However, thrombin and thrombin receptors also play a major role in atherosclerosis and arterial thrombosis, leading to strokes, myocardial infarcts and other forms of cardiovascular disease. Accordingly, considerable research is being performed to identify and develop drugs that can prevent that activation of thrombin receptors, particularly on platelets.

A number of assays are currently available for indirect determination of thrombin activation by measuring platelet response to thrombin. Examples of such assays include: 1) thrombin-induced platelet aggregation, 2) thrombin-induced secretion of platelet storage granule contents such as serotonin, and 3) detection by flow cytometry of thrombin-induced expression of activation-dependent antigens on the platelet surface, such as P-selectin or activated fibrinogen receptors. However, all of these assays require the use of fresh human platelets. Thus, as drug screening assays they are limited by platelet sensitivity to the dimethyl sulfoxide in which many test compounds must be suspended. Further, none of these assays specifically measure activation of the one thrombin receptor that has been cloned to date. Accordingly, these assays do not appear to be receptor specific.

Thus, an assay for rapid screening of large compound libraries for potential thrombin receptor antagonists is needed.

SUMMARY OF THE INVENTION

An object of the present invention is to provide an assay for thrombin receptor activation which can be used to identify thrombin receptor antagonists. The assay of the present invention comprises exposing non-adherent megakaryoblastic cells to a labeled thrombin receptor antibody, incubating the cells with an agonist peptide which activates the thrombin receptors on the cells so that the antibody-receptor complex is internalized by the cell, and measuring cell-associated label after antibody that has not been internalized has been stripped from the cell surface. Thrombin receptor antagonists can be identified by comparing the amount of receptor internalized by cells exposed to the thrombin receptor agonist in the presence and absence of the potential antagonist. This assay has a number of advantages over prior art assays for receptor activation including adaptability for performance in a microtiter plate, high signal-to-noise ratio and relative insensitivity to the effects of dimethyl sulfoxide. Further, the assay of the present invention does not require human platelets, which must be obtained from fresh human blood, but rather utilizes cells that are easily grown in culture.

DETAILED DESCRIPTION OF THE INVENTION

A novel assay for measuring thrombin receptor activation and subsequent internalization has now been developed which can be used in the screening of potential antagonists of thrombin receptor activation. The internalization of activated thrombin receptors in the human megakaryoblastic HEL and CHRF-288 cell lines exposed to the peptide agonist SFLLRN (SEQ ID NO: 1) occurs within 5 minutes and is >90% complete. Although some of the internalized receptors are recycled back to the cell surface, this takes more than 1 hour. Replacement of the old receptors with new receptors takes up to 16 hours. Accordingly, the loss of thrombin receptors from the cell surface and internalization of these receptors can be used as an index of receptor activation. Thrombin receptor antagonists which prevent receptor activation will also prevent internalization of thrombin receptors exposed to the peptide agonist. Accordingly, thrombin receptor antagonists can be identified by a decrease in the internalization of thrombin receptors from the cell surface.

Figure 1:
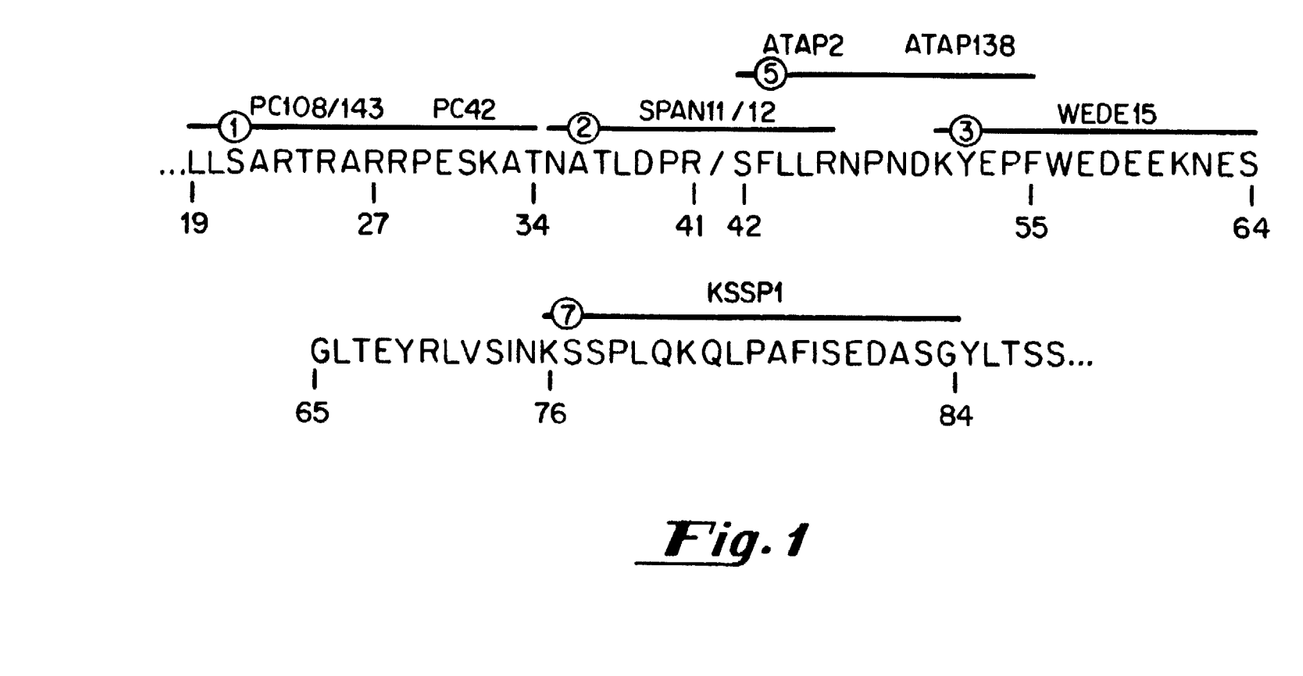
FIG. 1 provides the sequence of residues 19 through 84 of the human thrombin receptor (SEQ ID NO: 2) and indicates by bold lines labeled with circled numbers the portions of the receptor referred to as Peptide 1 (SEQ ID NO: 3), Peptide 2 (SEQ ID NO: 4), Peptide 3 (SEQ ID NO: 5), Peptide 5 (SEQ ID NO:6) and Peptide 7 (SEQ ID NO:7) and the cleavage site between residues 41 and 42. Antibody labels PC108/143, PC42, SPAN11/12, ATAP2, ATAP138, WEDE15, and KSSP1 mark the approximate location of the antibody epitopes based upon ELISA results with these peptides.

A library of monoclonal antibodies directed against epitopes within the N-terminus of the human thrombin receptor have now been developed. A number of these antibodies remain associated with activated thrombin receptors when they are internalized. See FIG. 1. Neither the rate of internalization nor the initial intracellular distribution of the internalized receptors appear to be affected by the presence of the antibody. Using these antibodies, a thrombin receptor assay has now been developed wherein activation of the thrombin receptor by its peptide agonist is determined by measuring the internalization of labeled antibody. Molecules that act as antagonists of receptor activation can be identified in this assay by measuring a decrease in the amount of labeled antibody internalized by the cell. In a preferred embodiment, the antibody used in the assay is radiolabeled with a nuclide such as $^{125}$I. However, other detectable labels such as enzymes, fluorescent compounds, chemiluminescent compounds, and bioluminescent compounds can be used.

Cells which can be used in the present invention are those which express high levels of thrombin receptors, internalize greater than 90% of the activated receptors and grow easily in culture. Examples include, but are not limited to, CHRF cells and HEL cells. In a preferred embodiment, the assay of the present invention is performed with non-adherent megakaryoblastic cells such as CHRF-288 cells. These cells express approximately 200,000 copies of the human thrombin receptor per cell. The cells are placed in a sample holder such as a test tube or microtiter well plate. Typically, 10⁶ cells/ml are used. The cells are then exposed to a labeled thrombin receptor antibody for approximately 10 to 15 minutes. Concentrations of antibody of approximately 1 μg/ml have been found to be sufficient. An agonist peptide is then added and the cells are incubated for a short period of time, i.e., about 15 minutes. By "agonist peptide" it is meant a peptide which mimics thrombin by activating the thrombin receptors. In a preferred embodiment, the agonist peptide comprises the peptide SFLLRN (SEQ ID NO: 1). A concentration of approximately 10 μM of this agonist peptide has been found to be sufficient to activate the receptors. Incubations at room temperature and 37° C. have been demonstrated to be equivalent. Following incubation, the cells are washed at a neutral pH to remove unbound antibody and at an acidic pH to strip antibody remaining bound to the cell surface, i.e., not internalized. The amount of cell-associated labeled antibody is then determined. In a preferred embodiment, wherein the antibody is radiolabeled, the amount of cell-associated antibody internalized can be measured by scintillation counting of the cells. In another embodiment, antibody that is internalized with the receptor is detected colorimetrically. In this embodiment, after washing the cells at low pH to remove antibody on the cell surface, the cells are lysed, releasing internalized antibody. This antibody is then captured in a microtiter well plate coated with the peptide against which the antibody was raised. Bound antibody in the well is detected using an alkaline phosphatase or HRP-conjugated secondary antibody and a chromogenic substrate. Alternative detectable labels for the antibody and means for detecting internalized labeled antibody will be obvious to those skilled in the art upon this disclosure.

Using the assay of the present invention, molecules suspected of being thrombin receptor antagonists can be screened for their ability to inhibit thrombin receptor activation and internalization of the thrombin receptors. molecules which are thrombin receptor antagonists are identified by first exposing non-adherent megakaryoblastic cells to a labeled thrombin receptor antibody so that the labeled thrombin receptor antibody binds to thrombin receptors on the cells to form an antibody-receptor complex. The cells are then contacted with a molecule suspected of being a thrombin receptor antagonist. An agonist peptide which activates the thrombin receptors on the cells is then added and the cells are incubated so that the antibody-receptor complex is internalized by the cell. In a preferred embodiment, molecules to be screened are introduced into the assay approximately 5 minutes before the agonist peptide. The cells are then washed to remove any antibody remaining on the surface of the cells and the amount of labeled antibody in the cells is determined. This amount of labeled antibody in the cells contacted with the molecule is compared to an amount in control cells. By "control cells" it is meant cells which are exposed to the labeled antibody and incubated with the peptide agonist but which are not exposed to the molecule. Molecules which are thrombin receptor antagonists will cause a decrease in the amount of labeled antibody in the cells as compared to control cells.

Figure 2:
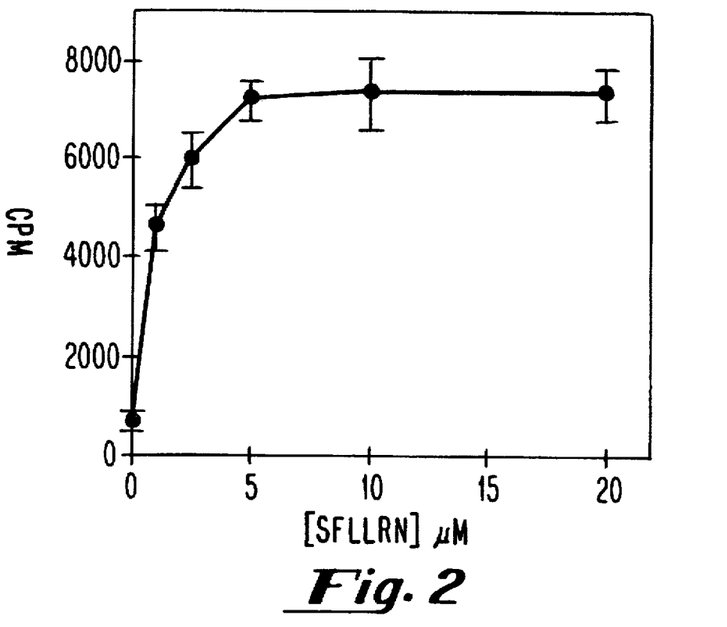
FIG. 2 is a linegraph showing the amount of radiolabeled antibody-thrombin receptor complex as determined by counts per minute (CPM) internalized in CHRF-288 cells by increasing amounts (μM) of the peptide agonist SFLLRN (SEQ ID NO: 1).
Figure 3:
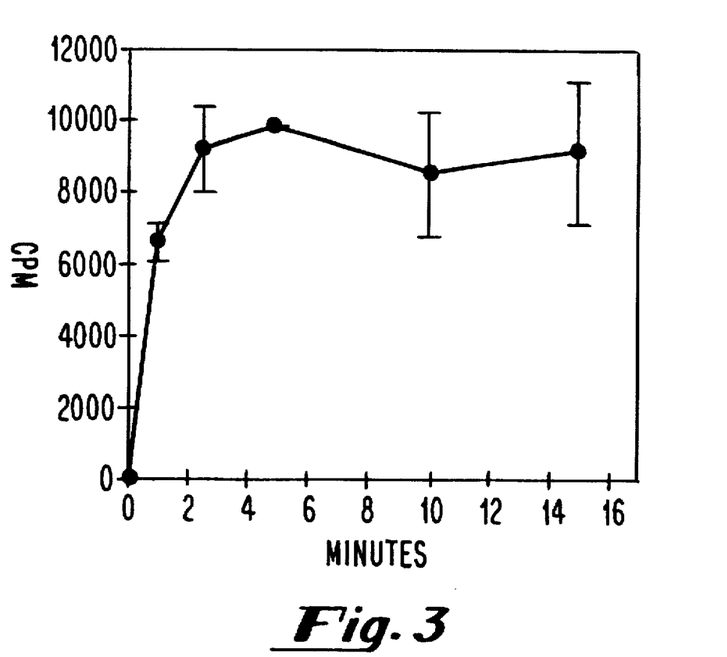
FIG. 3 is a linegraph showing the amount of radiolabeled antibody-thrombin receptor complex as determined by CPM internalized in CHRF-288 cells exposed to 10 μM SFLLRN (SEQ ID NO:1) over time in minutes.

A dose response curve for the internalization of radiolabeled-antibody/receptor complexes by the agonist peptide SFLLRN (SEQ ID NO: 1) was determined (FIG. 2). Internalization of the radiolabeled-antibody/receptor complex was half-maximal at 1 μM SFLLRN (SEQ ID NO: 1) which is consistent with previous reports of the concentration of peptide required for activation of the receptor alone. Vassallo et al. J. Biol. Chem. 1992 267, 6081-6085. Accordingly, formation of the complex does not alter the concentration of peptide required for activation of the receptor. The signal to noise ratio of this assay, determined as the ratio of counts per minute associated with the cell in the presence and absence of maximally effective peptide concentrations, is approximately 10:1. The time course of internalization of the radiolabeled-antibody complex in response to peptide SFLLRN (SEQ ID NO: 1) was also determined. See FIG. 3. Maximal internalization is reached within 5 minutes, a time consistent with internalization of the receptor alone. Thus, formation of the antibody-receptor complex does not alter the behavior of the receptor.

Figure 4:
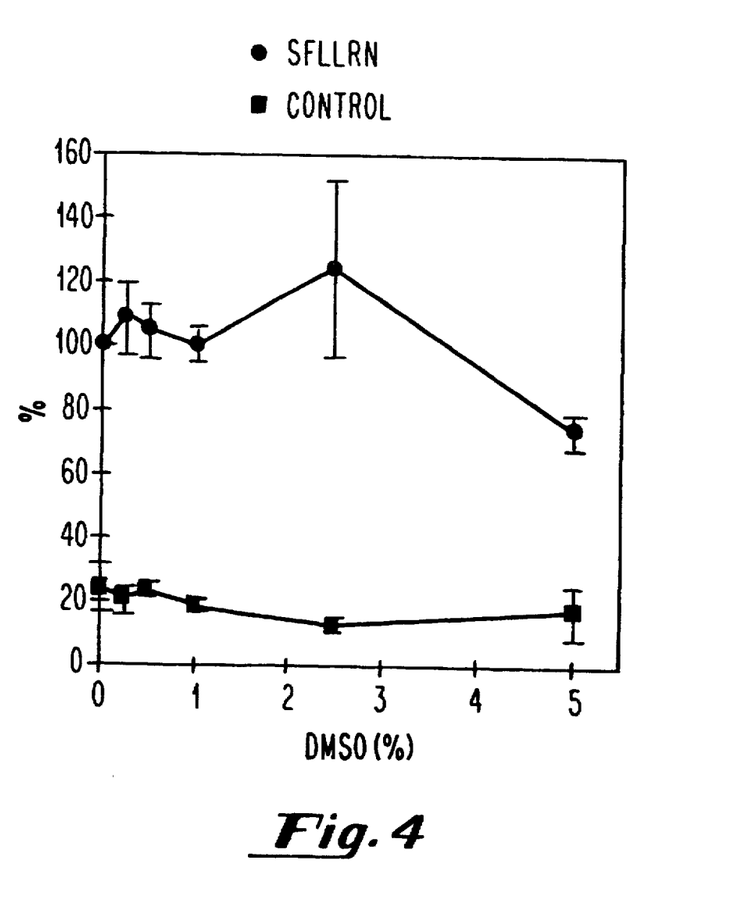
FIG. 4 is a linegraph showing the effects of increasing concentrations of dimethyl sulfoxide on the internalization of radiolabeled antibody-thrombin receptor complex in the presence of 10 μM SFLLRN (SEQ ID NO: 1) (depicted as filled diamonds) and in control cells not exposed to the peptide (depicted as filled squares)

Since many potential thrombin receptor antagonists require dissolution in dimethyl sulfoxide (DMSO) rather than an aqueous solution, the effects of DMSO on SFLLRN-induced internalization were assessed. Typically, final DMSO concentrations in the assay would be expected to be ≦1%. However, as shown in FIG. 4, the assay of the present invention is relatively unaffected even at concentrations of DMSO as high as 5%.

The following nonlimiting examples are provided to further illustrate the assay of the present invention.

EXAMPLES

Example 1: Production of Monoclonal Antibodies

Mice were immunized with Peptide 1 (SEQ ID NO: 3), Peptide 2 (SEQ ID NO: 4), Peptide 3 (SEQ ID NO: 5), Peptide 5 (SEQ ID NO: 6) or Peptide 7 (SEQ ID NO: 7) (See FIG. 1) conjugated to KLH using glutaraldehyde. This immunization was followed by two subsequent booster injections. The mice were then bled and their serum was tested by ELISA for anti-peptide activity. Mice testing positive were given another booster injection. The spleens were then removed and hybridomas were formed by standard methods. The hybridoma supernatants were screened by ELISA against Peptides 1, 2, 3, 5 and 7. Those testing positive were then screened for their ability to bind to thrombin receptors expressed on the surface of untreated megakaryoblastic cells such as HEL cells (ATCC catalog

TIB180) or CHRF-288 cells but not bind to the same cells following incubation with thrombin or to lymphoid cells that do not normally express thrombin receptors. Antibodies produced include PC108/143, PC42, SPAN11/12, ATAP2, ATAP138, WEDE15, and KSSP1.

Example 2: Preparation of $I^{125}$ labeled antibody PC108

Approximately 650 μg of PC108 in about 500 μl 50 mM phosphate buffer (pH 7.3) was mixed with 0.5 mCi radio-iodine followed by the addition of 50 μl of freshly prepared chloramine T (0.5 g/ml in potassium phosphate buffer, pH 7). The reaction was allowed to proceed for 30 seconds at room temperature and then stopped by the addition of sodium metabisulfate (50 μl of 1.25 mg.ml solution in phosphate buffer, pH 7). The reaction mixture was applied to a PD-10 column to separate the antibody from unmodified iodine. Using phosphate buffered saline as eluent, 0.5 ml fractions were collected and the fractions were counted for radioactivity. The void volume which contains the iodinated antibody was pooled and dialyzed exhaustively to remove any free iodine. The dialyzed antibody was stored at 4° C. The specific activity of the preparation was determined using the protein concentration estimated from its absorbance at 280 nm and the radioactivity of an aliquot of antibody.

Example 3: Evaluation of the Activity of Radio-iodinated PC108

The activity of the antibody was evaluated using an ELISA procedure where the ability of the modified antibody to bind to a peptide coated 96-well plate was compared with unmodified antibody of similar concentration. The antibody was detected using goat-anti mouse alkaline phosphate conjugate with ATTOPHOS (J.B.L., St. Luis Obispo, California) as the substrate that yields a fluorescent product which is measured using a fluorescence plate reader.

Example 4: Preparation of 96-well filtration plate for assay

A 96-well fiber glass plate (MILLIPORE Multiscreen 96-well plate, Cat No. MAFC NOB 10, Millipore Corp., Bedford, MA) was wetted by pipetting 100 μl PBS in each well, and pulling the vacuum after 1 minute incubation via a MILLIPORE Filtration system vacuum manifold. This procedure was repeated with 100 μl of superblock blocking buffer (Cat. No. 37515, Pierce, Rockford, IL) with a 5 minute incubation to block all non-specific binding sites. The wells were then rinsed with 250 μl of PBS and filtered by suction as before.

Example 5: Optimized Assay

Harvested CHRF cells were washed to remove excess medium using binding buffer (containing 10 ml of 10X RPM, 90 ml water, 1 ml 1 M HEPES, 1 ml 20° BSA, adjusted to pH 7.3–7.4) and re-suspended to yield a cell density of $4 \times 10^6$ cells/ml. With the 96-well plate positioned in the vacuum manifold, 250 μl of cell suspension (corresponding to about $10^6$ cells) was pipetted per well. One microgram of radio-iodinated antibody was then added to each well and the cells were mixed with the antibody. The antibody was allowed to bind to the receptor during a 5 minute incubation at room temperature. The peptide agonist SFLLRN (SEQ ID NO: 1) was then added in an amount such that a final concentration of 10 μM is achieved. The cells were again mixed and incubated for 10 minutes at room temperature. The contents of the wells were filtered by vacuum suction and 250 μl of ice-cold wash buffer (containing 10 ml of 10×RPMI, 90 ml water, 1 ml 1M MES, and 1 ml of 20% BSA, adjusted to pH 2.5) were then added to each well and incubated for 3 minutes before filtration. This was followed by washing with 250 μl of binding buffer. These two washing steps were then repeated. The radioactivity in the wells was quantitated after addition of 25 μl of scintillation fluid to each well using a WALLAC gamma counter (Wallac, Inc. Gaithersburg, Md.).

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 6
        ( B ) TYPE: Amino Acid
        ( D ) TOPOLOGY: Linear     ( x i ) SEQUENCE DESCRIPTION: SEQ ID NO: 1:

```
SER PHE LEU LEU ARG ASN
 1                   5
```

( 2 ) INFORMATION FOR SEQ ID NO:2:

( i ) SEQUENCE CHARACTERISTICS:
        ( A ) LENGTH: 76
        ( B ) TYPE: Amino Acid
        ( D ) TOPOLOGY: Linear     ( x i ) SEQUENCE DESCRIPTION: SEQ ID NO: 2:

```
LEU LEU SER ALA ARG THR ARG ALA ARG ARG
 1               5                   1 0
PRO GLU SER LYS ALA THR ASN ALA THR LEU
```

```
                        15                      20
ASP PRO ARG SER PHE LEU LEU ARG ASN PRO
                25                      30
ASN ASP LYS TYR GLU PRO PHE TRP GLU ASP
                35                      40
GLU GLU LYS ASN GLU SER GLY LEU THR GLU
                45                      50
TYR ARG LEU VAL SER ILE ASN LYS SER SER
                55                      60
PRO LEU GLN LYS GLN LEU PRO ALA PHE ILE
                65                      70
SER GLU ASP ALA SER GLY
                75
```

( 2 ) INFORMATION FOR SEQ ID NO:3:

( i ) SEQUENCE CHARACTERISTICS:
        ( A ) LENGTH: 16
        ( B ) TYPE: Amino Acid
        ( D ) TOPOLOGY: Linear     ( x i ) SEQUENCE DESCRIPTION: SEQ ID NO: 3:

```
LEU LEU SER ALA ARG THR ARG ALA ARG ARG
1               5                       10
PRO GLU SER LYS ALA THR
                15
```

( 2 ) INFORMATION FOR SEQ ID NO:4:

( i ) SEQUENCE CHARACTERISTICS:
        ( A ) LENGTH: 13
        ( B ) TYPE: Amino Acid
        ( D ) TOPOLOGY: Linear     ( x i ) SEQUENCE DESCRIPTION: SEQ ID NO: 4:

```
ASN ALA THR LEU ASP PRO ARG SER PHE LEU
1               5                       10
LEU ARG ASN
```

( 2 ) INFORMATION FOR SEQ ID NO:5:

( i ) SEQUENCE CHARACTERISTICS:
        ( A ) LENGTH: 14
        ( B ) TYPE: Amino Acid
        ( D ) TOPOLOGY: Linear     ( x i ) SEQUENCE DESCRIPTION: SEQ ID NO: 5:

```
LYS TYR GLU PRO PHE TRP GLU ASP GLU GLU
1               5                       10
LYS ASN GLU SER
```

( 2 ) INFORMATION FOR SEQ ID NO:6:

( i ) SEQUENCE CHARACTERISTICS:
        ( A ) LENGTH: 14
        ( B ) TYPE: Amino Acid
        ( D ) TOPOLOGY: Linear     ( x i ) SEQUENCE DESCRIPTION: SEQ ID NO: 6:

```
SER PHE LEU LEU ARG ASN PRO ASN ASP LYS
1               5                       10
TYR GLU PRO PHE
```

(  2  ) INFORMATION FOR SEQ ID NO:7:

(  i  ) SEQUENCE CHARACTERISTICS:
        ( A ) LENGTH: 19
        ( B ) TYPE: Amino Acid
        ( D ) TOPOLOGY: Linear     (  x i  ) SEQUENCE DESCRIPTION: SEQ ID NO: 7:

```
LYS  SER  SER  PRO  LEU  GLN  LYS  GLN  LEU  PRO
1                   5                        10
ALA  PHE  ILE  SER  GLU  ASP  ALA  SER  GLY
                    15
```

What is claimed is:

1. A method of measuring thrombin receptor activation comprising:

(a) exposing non-adherent megakaryoblastic cells which express thrombin receptors to a labeled thrombin receptor antibody specific for SEQ ID NO: 2 or so that the labeled thrombin receptor antibody binds to thrombin receptors on the cells to form an antibody-receptor complex;

(b) incubating the cells with an agonist peptide comprising SEQ ID NO: 1 which activates the thrombin receptors on the cells so that the antibody-receptor complex is internalized by the cell;

(c) washing the cells to remove any antibody remaining on the surface of the cells; and (d) measuring labeled antibody internalized by the cells which is an index of thrombin receptor activation.

2. The method of claim 1 wherein step b) further comprises contacting the cells with a molecule suspected of being a thrombin receptor antagonist prior to incubation with the agonist peptide and step d) further comprises comparing the measured amount of labeled antibody internalized by the cells contacted with the molecule to control cells to identify molecules which are thrombin receptor antagonists by a decrease in measured thrombin receptor activation.

* * * * *

UNITED STATES PATENT AND TRADEMARK OFFICE
CERTIFICATE OF CORRECTION

PATENT NO. : 5,776,700
DATED : July 7, 1998
INVENTOR(S) : Brass et al.

Page 1 of 2

It is certified that error appears in the above-identified patent and that said Letters Patent is hereby corrected as shown below:

At col 1, line 18, please delete "Arg$^4$" and insert therefor -- Arg$^{41}$--.

At col 3, line 20, please delete "906" and insert therefor --90%--.

At col 3, line 27, please delete "106" and insert therefor --10$^6$--.

At col 3, line 63, please delete "mol-" and insert therefor -- Mol- --.

UNITED STATES PATENT AND TRADEMARK OFFICE
CERTIFICATE OF CORRECTION

PATENT NO. : 5,776,700
DATED : June 22, 1998
INVENTOR(S) : Brass et al.

It is certified that error appears in the above-identified patent and that said Letters Patent is hereby corrected as shown below:

At col 5, line 15, please delete "mg.ml" and insert therefor --mg/ml--.

At col 6, line 17, please delete "20°" and insert therefor --20%--.

Signed and Sealed this

Twenty-second Day of December, 1998

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,776,700

DATED : July 7, 1998

INVENTOR(S) : Brass, et al.

It is certified that error appears in the above-identified patent and that said Letters Patent is hereby corrected as shown below:

On the title page, please delete "Thrombine" and insert therefor --Thrombin--.

At col 1, line 18, please delete "Arg$^4$" and insert therefor -- Arg$^{41}$--.

At col 3, line 20, please delete "906" and insert therefor -- 90%--.

At col 3, line 27, please delete "106" and insert therefor -- 10$^6$--.

At col 3, line 63, please delete "mol-" and insert therefor -- Mol- --.

UNITED STATES PATENT AND TRADEMARK OFFICE
CERTIFICATE OF CORRECTION

PATENT NO. : 5,776,700

DATED : July 7, 1998

INVENTOR(S) : Brass, et al.

It is certified that error appears in the above-identified patent and that said Letters Patent is hereby corrected as shown below:

At col 5, line 15, please delete "mg.ml" and insert therefor --mg/ml --.

At col 6, line 17, please delete "20°" and insert therefor --20%--.

This certificate supercedes Certificate of Correction issued December 22, 1998.

Signed and Sealed this

Eighth Day of August, 2000

Attest:

Attesting Officer

Q. TODD DICKINSON

Director of Patents and Trademarks